United States Patent [19]

Baldwin et al.

[11] 4,011,218

[45] Mar. 8, 1977

[54] 1,2,4-TRIAZOLES
[75] Inventors: John J. Baldwin, Lansdale; Frederick C. Novello, Berwyn, both of Pa.
[73] Assignee: Merck & Co., Inc., Rahway, N.J.
[22] Filed: Dec. 3, 1974
[21] Appl. No.: 529,151

Related U.S. Application Data

[63] Continuation of Ser. No. 269,684, July 7, 1972, abandoned, which is a continuation-in-part of Ser. No. 75,785, Sept. 25, 1970, abandoned.
[52] U.S. Cl. .................. 260/250 AH; 260/250 BN; 260/294.8 D; 260/256.4 R; 260/256.5 R; 260/296 R; 260/295 R; 424/270; 260/294.8 F; 260/295 AM
[51] Int. Cl.[2] ........................................ C07D 249/08
[58] Field of Search ............. 260/250 AH, 250 BN
[56] References Cited

UNITED STATES PATENTS

| | | | |
|---|---|---|---|
| 3,308,131 | 3/1967 | McKusick | 260/294 |
| 3,515,723 | 6/1970 | Cragoe | 260/250 BN |

FOREIGN PATENTS OR APPLICATIONS 1,092,359  11/1954  France ............................ 260/296

OTHER PUBLICATIONS

Gelhard et al., J. Organic Chem., vol. 30, pp. 318, & 319 (1965).

*Primary Examiner*—Donald G. Daus
*Assistant Examiner*—D. B. Springer
*Attorney, Agent, or Firm*—J. Jerome Behan; Daniel T. Szura

[57] ABSTRACT

Triazoles substituted at the 3 and 5 positions having an optional substituent in the 1 position are provided. Methods of preparing the novel substituted triazoles are described. The substituted triazoles are useful as anti-gout and anti-hyperuricemic agents. Compositions useful in the treatment of gout and hyperuricemia containing a substituted triazole as the active ingredient are also provided.

9 Claims, No Drawings

1,2,4-TRIAZOLES

This is a continuation of Ser. No. 269,684, filed July 7, 1972, which was a continuation-in-part of Ser. No. 075,785, filed Sept. 25, 1970, both now abandoned.

BACKGROUND OF THE INVENTION:

1. Field of the Invention

The invention relates to a class of triazoles which are substituted in the 3 and 5 positions and bear optional substituents in the 1 position. The substituent in the 1 position is an alkyl, alkanoyl, carbamoyl or benzyl group. The substituents in the 3 and 5 positions are aryl or heteroaryl groups, or a group derived therefrom.

2. Description of the Prior Art

The herein-described substituted triazoles have utility as anti-gout and anti-hyperuricemic agents.

Gout is a condition affecting humans and lower animals, particularly birds and reptiles, which is characterized by perversion of the purine metabolism resulting in an excess of uric acid in the blood, by attacks of acute arthritis, and by formation of chalky deposits in the cartilages of the joints. These deposits are made up chiefly of urates, or uric acid. Hyperuricemia is a condition characterized by an excess of uric acid in the blood.

Uric acid serves no biochemical function in the body and is merely an end product of purine metabolism. It is well known in the art that the purine bases adenine and guanine, which play key roles in a wide variety of chemical processes, both give rise to uric acid in the body. Adenylic acid and guanylic acid are converted to the free purine bases by destructive metabolic enzymes. A portion of the free purine bases is converted to purine ribonucleotides and the remainder is degraded to the free bases xanthine and hypoxanthine. A single enzyme, xanthine oxidase, converts both xanthine and hypoxanthine to uric acid for excretion.

Although human purine biosynthesis can be inhibited at the stage of formyl glycinimide ribotide by the glutamine antagonists azaserine and 6-diazo-5-oxo-1-norleucine, a high incidence of undesirable side effects precludes their being used clinically for this purpose. In recent years, substantial progress has been made in attempting to control the excessive levels of uric acid in patients afflicted with gout through the use of pharmaceutical agents. Uric acid synthesis has been effectively blocked by the use of allopurinol, 4-hydroxypyrazolo-[3,4-d]-pyrimidine, a compound which is a structural isomer of hypoxanthine. Allopurinol acts as a specific inhibitor of the enzyme xanthine oxidase, which is responsible for the conversion of both hypoxanthine and xanthine to uric acid. As a direct result of the administration of this compound to patients afflicted with gout, part of the uric acid which would normally end up in the urine is replaced instead by the oxypurines, hypoxanthine and xanthine, thus greatly reducing the content of uric acid in serum and urine. Azathioprine has also been employed in patients afflicted by gout to inhibit the excessive purine synthesis, which tends to produce abnormal amounts of uric acid. Other compounds, such as acetylsalicylic acid, thiophenylpyrazolidine, and phenylbutazine have been employed in the treatment of gout. Many of the existing compounds used in the treatment of gout, however, relieve the inflammation and other symptoms connected therewith but have no effect on the conditions which give rise to gouty arthritis or hyperuricemia. Thus, there is still a need for compounds which can be employed in the prophylactic treatment of gout as well as for the treatment of other abnormal conditions associated with hyperuricemia.

The substituted triazoles which are the subject of this invention have been found to be effective anti-gout and anti-hyperuricemic agents in that they will inhibit the action of the enzyme xanthine oxidase and thus reduce the content of uric acid in serum and urine. In addition to their use as anti-gout and anti-hyperuricemic agents, certain of the triazoles exhibit diuretic and hypotensive activity.

SUMMARY OF THE INVENTION

An object of this invention is to provide novel substituted 1,2,4-triazoles which are useful anti-gout, anti-hyperuricemic and hypotensive agents. Methods of preparing the novel substituted triazoles are described. Also within the scope of the invention are the alkali metal and alkaline earth metal salts of the triazoles, and in those cases where the substituent in the 3 or 5 position contains at least one basic nitrogen, the pharmaceutically acceptable quaternary and acid addition salts.

DESCRIPTION OF THE PREFERRED EMBODIMENTS

The novel 1,2,4-triazoles which are the subject of this invention may be depicted as follows:

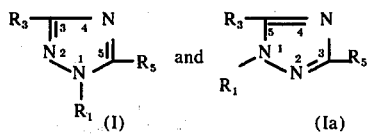

wherein
$R_1$ is hydrogen, lower alkyl, lower alkanoyl, aralkyl, for example, benzyl or menaphthyl and the like, carbamoyl, lower alkyl carbamoyl or di- lower carbamoyl;

$R_3$ is phenyl, naphthyl, as for example, 1-naphthyl or 2-naphthyl and the like, pyridylmethyl, as for example, picolyl, a five or six membered heterocycle containing from 1-3 oxygen, nitrogen or sulfur atoms as, for example, quinolyl, cinnolyl, pyridyl, pyrazinyl, furyl, pyrimidinyl, pyridazinyl, or thienyl, or substituted phenyl containing from 1-3 substituents selected from halogen, such as chlorine, bromine or iodine, lower alkyl as, for example, methyl, ethyl or propyl and the like, amino, di- lower alkylamino wherein the lower alkyl moiety contains from 1-5 carbon atoms as, for example, methyl, ethyl, propyl, butyl or pentyl and the like, sulfamoyl, lower alkylsulfamoyl as, for example, methanesulfamoyl or ethanesulfamoyl and the like, lower alkoxy as, for example, methoxy, ethoxy or propoxy and the like, or lower alkanoylamino as, for example, formamido, acetamido, propionamido or butyramido and the like, and $R_5$ is pyridyl, such as 2-pyridyl, 3-pyridyl or 4-pyridyl, pyrimidinyl or pyrazinyl; provided, that when $R_5$ is pyridyl $R_3$ is other than pyridyl, phenyl or alkylphenyl.

When the compounds of this invention contain a lower alkyl radical, it is preferred that such radical contain from 1-5 carbon atoms such as methyl, ethyl, propyl, butyl or pentyl and the like; lower alkanoyl radicals preferably contain from 2–5 carbons, examples being acetyl, propionyl, butyryl or valeryl and the like.

Also within the scope of the present invention are the alkali metal and alkaline earth metal salts of those triazoles where $R_1$ is hydrogen, such as the sodium, potassium, and calcium salts, and the pharmaceutically acceptable quaternary salts such as the methiodides and ethiodides, mineral acid salts such as the hydrochloride or sulfate salts of those compounds wherein the substituent in the 3 and/or 5 position contains at least one basic nitrogen, such as a pyridine ring. Also contemplated by the invention are the N-oxides of a nitrogen heterocycle substituent in the 3 or 5 position.

The following class of products are particularly effective xanthine oxidase inhibitors and, therefore, represent a preferrred embodiment of this invention:

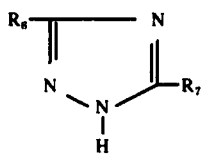

(Ib)

wherein $R_6$ is pyridyl, pyrazinyl, pyrimidinyl, pyridazinyl, quinolyl, furyl, thienyl, halophenyl, for example, 3-chlorophenyl or 4-chlorophenyl and the like, dihalophenyl, for example, 3,4-dichlorophenyl or 3,5-dichlorophenyl and the like, or halo- and dihalosulfamoylphenyl, for example, 3-sulfamoyl-4-chlorophenyl, or 3,4-dichloro-5-sulfamoylphenyl and the like and $R_7$ is pyridyl, pyridylmethyl, pyrimidinyl or pyrazinyl, with the proviso that when $R_6$ is pyridyl $R_7$ is other than pyridyl. The above products and the non-toxic salts thereof, including the alkali metal and alkaline earth metal salts, are especially effective anti-gout and antihyperuricemic agents and, therefore, represent a preferred subclass of compounds within the scope of this invention.

Those compounds corresponding to Formula Ib wherein $R_7$ is pyridyl, pyrazinyl or pyrimidinyl, and $R_6$ is halophenyl, dihalo-sulfamoylphenyl, thienyl, pyrazinyl, furyl, quinolyl, pyrimidinyl or pyridazinyl represent an especially preferred subclass of compounds within the scope of the present invention. Most preferred among the preferred compounds are those wherein $R_7$ is pyridyl and $R_6$ is halophenyl.

In addition to their utility as anti-gout and antihyperuricemic agents, the following products are useful as diuretics and hypotensive agents:

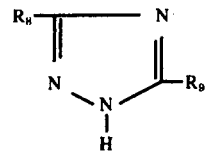

wherein $R_8$ is halophenyl or dihalophenyl, as for example, 3-chlorophenyl, 4-chlorophenyl or 3,4-dichlorophenyl and the like and $R_9$ is pyridyl. The above-described products are characterized by their ability to reduce the concentration of sodium and chloride ions in the body, lower dangerous excesses of fluid levels to acceptable limits and, in general, alleviate conditions usually associated with edema.

The compounds of Formulas I and Ia can be prepared by a series of reactions which are depicted in the following flow diagram:

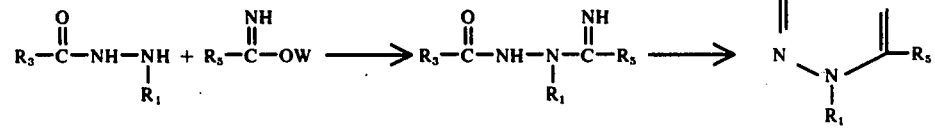

(I)

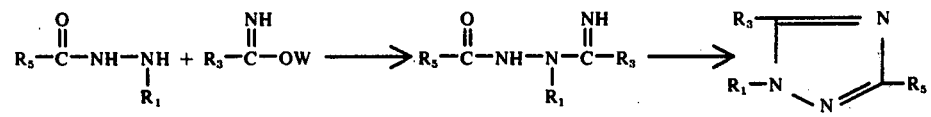

(Ia)

wherein $R_1$ is hydrogen or loweralkyl and $R_3$ and $R_5$ are as defined above, and W is loweralkyl wherein the alkyl group contains 1–5 carbons. As will be appreciated by those skilled in this art, Compounds I and Ia are the same when $R_1$ is hydrogen.

As can be seen from the above reaction diagram, a substituted hydrazine compound such as, for example, isonicotinoylhydrazine, is reacted with an imino ester such as, for example ethyl p-chloroiminobenzoate, in a suitable solvent. Either lower boiling solvents, such as methanol or ethanol, or nitromethane, or high boiling solvents, such as decalin, xylene, or dimethylsulfoxide, may be employed. When low boiling solvents are employed, the product of the reaction is usually the intermediate acylamidrazone. A reaction time of 3–20 hours at temperatures of from room temperature to the reflux temperature of the solvent is employed. The intermediate acylamidrazone II (III) may be converted to I (Ia) by heating it in the absence of solvent at temperatures between 125°–300° C. for from about 15 minutes to one hour or in higher boiling solvents at or near the reflux temperature of the solvent for from about 1 to 20 hours. The final cyclized product is isolated and purified by techniques known in the art.

When high boiling solvents are employed, the reaction is conveniently carried out at or near the reflux temperature of the solvent. The preferred temperature range is between 100°–200° C. The reaction time is dependent upon the particular temperature range employed. The reaction is carried out without isolation of the intermediate and the final cyclized product is isolated and purified by techniques known in the art. For example, the product may be crystallized from a suitable solvent, such as methanol or ethanol. As can be seen from the above reaction diagram, where $R_1$ is loweralkyl, the selection of the particular hydrazine compound and the particular imino ester will depend upon which substituent is desired in the 3 and/or 5 position.

Alternatively, the 1,2,4-triazoles of this invention can be prepared by reacting a suitable carbonitrile such as, for example, 4-cyanopyridine, with an alkali metal, such as sodium or potassium in a lower alkanol to form the imino ester. The imino ester is then reacted with a suitable carboxylic acid hydrazide such as, for example, pyrazine carboxylic acid hydrazide, in a suitable solvent, such as methanol or ethanol. The reaction mixture is first heated, preferably at reflux temperatures, for from about ½ to 20 hours, after which the reaction mixture is concentrated by removal of the solvent, and the solid intermediate is heated at elevated temperatures, either in the presence or absence of solvent. When no solvent is employed, a temperature between 100°–300° C. for from about 15 minutes to 1 hour is preferred. The product is collected by techniques known in the art. Where high boiling solvents are employed, the reaction is conveniently carried out at or near the reflux temperature of the solvent. The preferred temperature range is 100°–200° C. The reaction time is dependent upon the particular temperature range employed.

Those compounds having a substituent other than hydrogen in the 1 position can also be prepared by reacting a triazole of Formula I where $R_1$ is hydrogen with an appropriate alkylating or acylating agent. Where $R_3$ and $R_5$ are different, a mixture of compounds is obtained, i.e. the substituent $R_1$ may be substituted on either one of the two adjacent nitrogens. For example, where the substituent is a loweralkanoyl group such as an acetyl or butyryl group, the triazole is reacted with a loweralkyl anhydride such as, for example, acetic anhydride or butyric anhydride. Where the substituent in the 1 position is an alkyl group, alkylation is achieved by reacting the sodium salt of the triazole with an alkylating agent such as, for example, dimethylsulfate. Alkylation of the 1,2,4-triazoles generally occurs in the 1 position. Where the alkyl group is a methyl group, methylation can be achieved by reacting the triazole with diazomethane in a suitable solvent, such as diethylether.

Those compounds wherein the substituent in the 1 position is a carbamoyl or substituted carbamoyl group are prepared by reacting a 3,5-substituted-1,2,4-triazole with a carbamoyl halide such as, for example, dimethylcarbamoyl chloride in a suitable solvent such as tetrahydrofuran in the presence of a base, such as, for example, sodium hydride.

An alternate method for preparing those compounds having an alkyl group in the 1 position consists of first reacting a nitrile, such as, for example, 4-cyanopyridine, with an alkali metal, such as sodium, in an alcoholic solvent, such as methanol, at room temperature and adding to this solution a hydrazide, such as, for example, a 1-isonicotinoyl-2-loweralkylhydrazine. The reaction is heated, generally at reflux temperature, for about 3–20 hours. Depending upon the nature of the substituent, the final cyclized product is obtained directly or the intermediate acylamidrazone is obtained. In the case where the intermediate is obtained, it may be heated without solvent at about 100°–300° C. for from about 15 minutes to several hours, or the intermediate can be heated in a high boiling solvent such as xylene or decalin at about 100°–200° C. for about 1–20 hours. The alkylated triazole is isolated by techniques known in the art.

Those compounds of this invention which are amine oxides can be prepared by the method described above by employing a nitrile-N-oxide such as, for example, 4-cyanopyridine-N-oxide, as the nitrile reactant, or a hydrazine, such as pyridine-N-oxide-4-carboxylic acid hydrazide.

Representative examples of the compounds within the scope of this invention are:
3-(p-chlorophenyl)-5-(4-pyridyl)-1,2,4-triazole,
3-pyrazinyl-5-(4-pyridyl)-1,2,4-triazole,
3-(3,4-dichlorophenyl)-5-(4-pyridyl)-1,2,4-triazole,
1-ethyl-3,5-di(4-pyrimidyl)-1,2,4-triazole,
3-(6-quinolyl)-5-(4-pyridyl)-1,2,4-triazole,
3-(2-furyl)-5-(4-pyridyl)-1,2,4-triazole,
3-(4-chloro-3-sulfamoylphenyl)-5-(4-pyridyl)-1,2,4-triazole,
3-(3,5-dimethoxyphenyl)-5-(4-pyridyl)-1,2,4-triazole,
3-(m-chlorophenyl)-5-(4-pyridyl)-1,2,4-triazole,
3-(p-bromophenyl)-5-(4-pyridyl)-1,2,4-triazole,
3-(2-naphthyl)-5-(4-pyridyl)-1,2,4-triazole,
3-(3,4-dichloro-5-sulfamoylphenyl)-5-(4-pyridyl)-1,2,4-triazole,
3,5-di(4-pyrimidyl)-1,2,4-triazole,
N-methyl-4-[3-(p-chlorophenyl)-1,2,4-triazolyl-5]-pyridiniumiodide,
N-methyl-4-[3-(m-chlorophenyl)-1,2,4-triazolyl-5]-pyridiniumiodide,
3-(p-chlorophenyl)-5-(4-pyridazinyl)-1,2,4-triazole,
1-butyryl-3-(p-chlorophenyl)-5-(4-pyridyl)-1,2,4-triazole,
1-acetyl-3-(3,4-dichlorophenyl)-5-(4-pyridyl)-1,2,4-triazole,
1-methyl-3-(3,5-dimethoxyphenyl)-5-(4-pyridyl)-1,2,4-triazole,
1-benzyl-3,5-di(4-pyrimidyl)-1,2,4-triazole,
3-(3,5-dimethoxyphenyl)-5-(2-pyrazinyl)-1,2,4-triazole,
3-(p-methoxyphenyl)-5-(3-pyridyl)-1,2,4-triazole,
3-(p-sulfamoylphenyl)-5-pyrazinyl-1,2,4-triazole,
1-methyl-3-(4-pyridyl)-5-(p-chlorophenyl)-1,2,4-triazole,
1-acetyl-3-(6-quinolyl)-5-(p-dimethylaminophenyl)-1,2,4-triazole,
and 1-methyl-3-(p-chlorophenyl)-5-(4-pyridyl)-1,2,4-triazole.

The substituted triazoles which are the subject of this invention inhibit the action of the enzyme xanthine oxidase resulting in a significant decrease in the concentration of uric acid in the blood and urine and are, therefore, capable of aborting attacks of gout.

For testing purposes, xanthine oxidase obtained from milk may be employed to demonstrate the ability of the substituted triazoles to inhibit the enzyme. The general procedure is to employ a 5–10 unit suspension of the enzyme per milliliter of 60% saturated ammonium sulfate of the enzyme; 1 unit of such a suspension converts 1 μmole of xanthine to uric acid per minute. Generally, for a 1-day assay, about 0.05 ml. of enzyme is diluted with about 3 ml. of buffer. As the buffer, tris buffer (0.05 mole, pH 7.4) may be employed. The inhibitor to be treated is dissolved in buffer or a suitable solvent, such as dimethylsulfoxide; the same solvent is used to dilute the solution. The buffer, hypoxanthine and solvent are placed in a cell, and the enzyme solution is then added, and the rate of increase in absorbance at 290mµ is noted with a recording spectrophotometer. Generally, sufficient enzyme is employed to give about 0.1 absorbance units change per minute, and sufficient inhibitor is used to give 30–70% inhibition. The $\mu$M concentration of inhibitor necessary for 50% inhibition ($V_0/V_1 = 2$) is determined by plotting $V_0/V_1$ against I, where $V_0$ = velocity without inhibitor, $V_1$ = velocity with inhibitor, and I = inhibitor concentration.

The therapeutically active substituted triazoles can be administered as the active ingredient in association with a pharmaceutically acceptable carrier in the form of tablets, elixirs, capsules, and the like. These preparations may be made by any of the known pharmaceutical methods. For example, in tablet form, they are compounded with an inert pharmaceutical carrier which may contain a suitable binder such as, for example, gums, starches, and sugars. They may also be incorporated into a gelatin capsule or formulated into elixirs which have the advantage of being susceptible to manipulations in flavor by the addition of standard natural or synthetic flavoring materials. The compound is generally administered in compositions which are so proportioned as to afford a unit dosage of about 30 mg. to 1.5 gm. per day. The preferred dosage level, however, is about 100–800 mg. per day.

The following examples serve to illustrate typical tablet, capsule, and elixir formulations incorporating the therapeutically active substituted triazoles of this invention:

FORMULATION I

| COMPRESSED TABLET COMPRISING 0.5 GM. OF ACTIVE INGREDIENT | |
|---|---|
| INGREDIENT | AMOUNT - MG. |
| 3-(p-chlorophenyl)-5-(4-pyridyl)-1,2,4-triazole | 500.0 |
| Starch paste - 12½%, 100 cc allow. | 12.5 |
| | 512.5 |
| Starch, U.S.P. Corn | 25.0 |
| Magnesium stearate | 5.5 |
| | 543.0 |

The 3-(p-chlorophenyl)-5-(4-pyridyl)-1,2,4-triazole is granulated with the starch paste and while moist passed through a No. 14 screen, dried at 45° C. for 20 hours, and then passed 3 times through a No. 14 screen. The starch is then passed through a No. 90 bolting cloth onto the granulation, and all ingredients are blended thoroughly. The magnesium stearate is passed through a No. 90 bolting cloth onto the granulation, and these ingredients are blended, after which the granulation is compressed into tablets using a 14/32 inch flat, bevelled, scored punch having a thickness of 0.205±0.005 inch yielding 1,000 tablets each weighing 0.543 grams.

FORMULATION II

| ENCAPSULATION - FOR 250 MG. CAPSULE | |
|---|---|
| INGREDIENT | AMOUNT - MG. |
| 3-pyrazinyl-5-(4-pyridyl)-1,2,4-triazole | 250 |
| Lactose | 93 |
| Talc | 7 |

Blend lactose, talc and the 3-pyrazinyl-5-(4-pyridyl)-1,2,4-triazole in suitable blending equipment, and encapsulate into a No. 2 capsule at a target weight of 350 mg.

FORMULATION III

| LIQUID SUSPENSION - FORMULA | |
|---|---|
| INGREDIENT | AMOUNT - g./l. |
| Veegum H.V. | 3.0 |
| Water | 150.0 |
| Methyl paraben | 1.0 |
| 1-methyl-5-(4-pyridyl)-3-(p-chlorophenyl)-1,2,4-triazole | 50.0 |
| Kaolin | 10.0 |
| Flavor | 1.0 |
| Glycerin, 9.5 to 1 liter | |

Suspend Veegum in water with vigorous agitation, add methyl paraben and allow to stand overnight to ensure complete hydration of Veegum. In separate vessel suspended 1-methyl-5-(4-pyridyl)-3-(p-chlorophenyl)-1,2,4-triazole in about 750 cc. of glycerin. Add kaolin and stir until homogeneous. Slowly add aqueous dispersion of Veegum and methyl paraben. Add flavor and continue agitation for 1 hour to ensure homogeneity. Q.S. with remaining glycerin to 1:1. Stir until homogeneous. 1 Teaspoonful contains 250 mg. of 1-methyl-5-(4-pyridyl)-3-(p-chlorophenyl)-1,2,4-triazole.

The following examples are given for purposes of illustration and not by way of limitation:

EXAMPLE 1

3-PYRAZINYL-5-(4-PYRIDYL)-1,2,4-TRIAZOLE

Sodium (0.4 grams) is added to pyridine-4-carbonitrile (8.3 grams, 0.08 mole) in methanol, and the solution is allowed to stand 30 minutes at room temperature. A suspension of pyrazine carboxylic acid hydrazide (9.6 grams, 0.07 mole) in methanol (160 ml.) is added, and the resulting solution is heated at reflux for 30 minutes. After cooling, the intermediate acylamidrazone is collected by filtration. The acyclic intermediate is then heated at 260° C. for 15 minutes, after which the reaction is cooled to room temperature. Upon recrystallization from acetonitrile-water, 3-pyrazinyl-5-(4-pyridyl)-1,2,4-triazole is obtained, m.p. 251°–252.5° C.

EXAMPLES 2 - 22

The following compounds are prepared by the reaction procedure described in Example 1:

| EXAMPLE | HYDRAZIDE | NITRILE | COMPOUND | MELTING POINT |
|---|---|---|---|---|
| 2 | 3,4-dichlorobenzoyl-hydrazine | 4-cyanopyridine | 5-(4-pyridyl(-3-(3,4-dichlorophenyl)-1,2,4-triazole | 345–346.5° C. |
| 3 | 6-quinolinecarboxylic acid hydrazide | 4-cyanopyridine | 5-(4-pyridyl)-3-(6-quinolyl)-1,2,4-triazole | 313–314.5° C. |
| 4 | 3-pyridyl acetic acid hydrazide | 4-cyanopyridine | 3-(3-picolyl)-5-(4-pyridyl)-1,2,4-triazole | 161–162° C. |

| EXAMPLE | HYDRAZIDE | NITRILE | COMPOUND | MELTING POINT |
|---|---|---|---|---|
| 5 | 2-furoic acid hydrazide | 4-cyanopyridine | 5-(4-pyridyl)-3-(2-furyl)-1,2,4-triazole | 216–217° C. |
| 6 | 4-chloro-3-sulfamoyl-benzoyl hydrazide | 4-cyanopyridine | 5-(4-pyridyl)-3-(4-chloro-3-sulfamoylphenyl)-1,2,4-triazole | 335.5–336.5° C. |
| 7 | 3,5-dimethoxy-benzoylhydrazine | 4-cyanopyridine | 5-(4-pyridyl)-3-(3,5-dimethoxyphenyl)-1,2,4-triazole | 252–253.5° C. |
| 8 | m-chlorobenzoyl-hydrazine | 4-cyanopyridine | 5-(4-pyridyl)-3-(m-chlorophenyl)-1,2,4-triazole | 269–271° C. |
| 9 | pyrazinecarboxylic acid hydrazide | 2-cyanopyridine | 5-(2-pyridyl)-3-pyrazinyl-1,2,4-triazole | 248–250° C. |
| 10 | isonicotinic acid hydrazide | 2-cyanopyrimidine | 5-(4-pyridyl)-3-(2-pyrimidinyl)-1,2,4-triazole | 274–276° C. |
| 11 | 3,5-dichlorobenzoyl-hydrazine | 4-cyanopyridine | 5-(4-pyridyl)-3-(3,5-dichlorophenyl)-1,2,4-triazole | 298–299.5° C. |
| 12 | p-bromobenzoyl-hydrazine | 4-cyanopyridine | 5-(4-pyridyl)-3-(p-bromophenyl)-1,2,4-triazole | 263–264° C. |
| 13 | 4-pyridazinecarboxylic acid hydrazide | 4-cyanopyridine | 5-(4-pyridyl)-3-(4-pyridazinyl)-1,2,4-triazole | 276–278° C. |
| 14 | p-methoxybenzoyl hydrazine | 4-cyanopyridine | 5-(4-pyridyl)-3-(p-methoxyphenyl)-1,2,4-triazole | 247–249° C. |
| 15 | 2-thiophenecarboxylic acid hydrazide | 4-cyanopyridine | 5-(4-pyridyl)-3-(2-thienyl)-1,2,4-triazole | 240–241.5° C. |
| 16 | p-sulfamoylbenzoyl-hydrazine | 4-cyanopyridine | 5-(4-pyridyl)-3-(p-sulfamoyl phenyl)-1,2,4-triazole | 301–302° C. |
| 17 | 2-naphthoic acid hydrazide | 4-cyanopyridine | 5-(4-pyridyl)-3-(2-naphthyl)-1,2,4-triazole | 289–390° C. |
| 18 | 3,4-dichloro-5-sulfamoylbenzoyl-hydrazine | 4-cyanopyridine | 5-(4-pyridyl)-3-(3,4-dichloro-5-sulfamoylphenyl)-1,2,4-triazole | 330° C.(dec.) |
| 19 | 2-pyridylacetic acid hydrazide | 4-cyanopyridine | 5-(4-pyridyl)-3-(2-picolyl)-1,2,4-triazole | 190–191° C. |
| 20 | isonicotinic acid hydrazide | 4-cyanopyrimidine | 5-(4-pyridyl)-3-(4-pyrimidinyl)-1,2,4-triazole | 285–286.5° C. |
| 21 | 4-pyrimidinecarboxylic acid hydrazide | 4-cyanopyrimidine | 3,5-di(4-pyrimidinyl)-1,2,4-triazole | 302–304° C. |
| 22 | 2,4-dichloro-5-sulfamoylbenzoyl-hydrazine | 4-cyanopyridine | 5-(4-pyridyl)-3-(2,4-dichloro-5-sulfamoylphenyl)-1,2,4-triazole | 297–299° C. |

EXAMPLE 23
3-(p-CHLOROPHENYL)-5-(4-PYRIDYL)-1,2,4-TRIAZOLE

To a suspension of isonicotinoylhydrazine (10.9 grams, 0.08 mole) in methanol (250 ml.) is added a solution of ethyl p-chloroiminobenzoate (14 grams, 0.08 mole) in methanol (50 ml.). The reaction mixture is refluxed for 30 minutes and is then concentrated until a solid separates out of solution. The mixture is then cooled, and the intermediate acylamidrazone is collected by filtration. The acyclic intermediate is then heated at 280° C. for 15 minutes, after which it is cooled to room temperature. Upon recrystallization from ethanol-water and sublimation, 3-(p-chlorophenyl)-5-(4-pyridyl)-1,2,4-triazole is obtained, m.p. 264.5°–265.5° C.

EXAMPLE 24
N-METHYL-4-[3-(p-CHLOROPHENYL)-1,2,4-TRIAZOLYL-5]-PYRIDINIUM IODIDE

To a suspension of 3-(p-chlorophenyl)-5-(4-pyridyl)-1,2,4-triazole (1 gram, 0.004 mole) in N,N-dimethylformamide (25 ml.) is added methyl iodide (1.4 grams, 0.01 mole), and the resulting solution is allowed to stand at room temperature for one hour. The solid which separates during the reaction is collected by filtration. Upon recrystallization from methanol, N-methyl-4-[3-(p-chlorophenyl)-1,2,4-triazolyl-5]-pyridinium iodide is obtained, m.p. 275° C.

When in the above procedure 3-(m-chlorophenyl)-5-(4-pyridyl)-1,2,4-triazole is employed in place of 3-(p-chlorophenyl)-5-(4-pyridyl)-1,2,4-triazole, N-methyl-4-[3-(m-chlorophenyl)-1,2,4-triazolyl-5]-pyridinium iodide is obtained, m.p. 280°–281° C.

EXAMPLE 25
3,5-DIPYRAZINYL-1,2,4-TRIAZOLE

Sodium (50 mg.) is added to 2-cyanopyrazine (1 gram, 0.01 mole) in 20 ml. of methanol. The solution is allowed to stand 1 hour at room temperature and is added to a suspension of pyrazine carboxylic acid hydrazide (1.4 grams, 0.01 mole) in 50 ml. of methanol. The reaction mixture is heated at reflux for 2 hours and then at room temperature for 16 hours. After cooling, the intermediate acylamidrazone is removed by filtration and is then heated at temperatures between 200° to 260° C. over 2½ hours. After cooling and recrystallization from methanol-water, 0.8 grams of 3,5-dipyrazinyl-1,2,4-triazole, m.p. 269°–270.5° C. is obtained.

EXAMPLE 26
1-ACETYL-3,5-DIPYRAZINYL-1,2,4-TRIAZOLE

A suspension of 3,5-dipyrazinyl-1,2,4-triazole (0.5 grams) in 20 ml. of acetic anhydride is heated on a steam bath for 17 hours. The resulting solution is filtered and concentrated to a solid. After recrystallization from benzene-hexane, 250 mg. of 1-acetyl-3,5-dipyrazinyl-1,2,4-triazole is obtained, m.p. 128°–130° C.

EXAMPLE 27
1-DIMETHYLCARBAMOYL-3,5-DIPYRAZINYL-1,2,4-TRIAZOLE

To 2.25 g. (0.01 mole) of 3,5-dipyrazinyl-1,2,4-triazole in 200 ml. of tetrahydrofuran is added 57% sodium hydride (.42 g., 0.01 mole). The reaction mixture is heated at reflux for one hour, cooled, and a solution of dimethylcarbamoyl chloride (1 gram, 0.01 mole) in 10 ml. of tetrahydrofuran is added dropwise. The reaction mixture is then refluxed 4 hours, cooled, filtered and concentrated to a solid. After recrystallization from benzene 1-dimethylcarbamoyl-3,5-dipyrazinyl-1,2,4-triazole is obtained.

EXAMPLE 28

3-(p-AMINOPHENYL)-5-(4-PYRIDYL)-1,2,4-TRIAZOLE

To 4-cyanopyridine (4.2 g.) in methanol (60 ml.) is added sodium (0.2 g.). The solution is allowed to stand for 0.5 hour at room temperature and is then added to a suspension of p-aminobenzhydrazide (6.4 g.) in 150 ml. of methanol. The resulting solution is heated 20 hours at reflux during which time a solid separates. The solid is filtered and heated to 245° C. over 1 hour and maintained at that temperature for an additional 15 minutes. After cooling the solid is recrystallized from a mixture of acetonitrile and water to yield 3-(p-aminophenyl)-5-(4-pyridyl)-1,2,4-triazole (2 g.) m.p. 251°–252.5° C.

Analysis calculated for $C_{13}H_{11}N_5$. Calculated: C,65.81; H,4.67; N,29.52. Found: C,65.95; H,4.71; N,29.61.

Upon substituting p-(dimethylamino)benzoylhydrazine and 3-cinnolylcarbohydrazine for p-aminobenzhydrazide in the above method and otherwise following the procedure described therein, there is thus obtained 3-(p-dimethylaminophenyl)-5-(4-pyridyl)-1,2,4-triazole and 3-(3-cinnolyl)-5-(4-pyridyl)-1,2,4-triazole.

EXAMPLE 29

3-(p-ACETYLAMINOPHENYL)-5-(4-PYRIDYL)-1,2,4-TRIAZOLE

To 3-(p-aminophenyl)-5-(4-pyridyl)-1,2,4-triazole (1 g.) is added acetic anhydride (20 ml.) and the resulting suspension is heated 18 hours on a steam bath. The excess acetic anhydride is removed under reduced pressure and water (25 ml.) is added to the residue. After stirring 0.5 hour, the solid is filtered and recrystallized to yield 3-(p-acetylaminophenyl)-5-(4-pyridyl)-1,2,4-triazole.

EXAMPLE 30

1-METHYL-3-(p-CHLOROPHENYL)-5-(4-PYRIDYL)-1,2,4-TRIAZOLE

To 4-cyanopyridine (2 g.) in methanol (30 ml.) is added sodium (0.1 g.). After standing at room temperature 0.5 hour the solution is added to 1-methyl-2-p-chlorobenzoylhydrazine (3.6 g.) in methanol (40 ml.). The reaction mixture is refluxed for 5 hours and concentrated to an oil which is solidified. After recrystallization from ethyl alcohol 0.5 g. of 1-methyl-3-(p-chlorophenyl)-5-(4-pyridyl)-1,2,4-triazole m.p. 191° C. is obtained.

Analysis calculated for $C_{14}H_{11}ClN_4$ Calculated: N,20.70; C,62.11; H,4.10 Found: N,20.66; C,62.07; H,4.06

Upon substituting 3-cyanopyridine for 4-cyanopyridine in the above method and otherwise following the procedure described therein there is thus obtained 1-methyl-3-(p-chlorophenyl)-5-(3-pyridyl)-1,2,4-triazole m.p. 157°–158.5° C.

Analysis calculated for $C_{14}H_{11}ClN_4$. Calculated: N,20.70; C,62.11; H,4.10. Found: N,20.61; C,62.12; H,4.10.

EXAMPLE 31

1-METHYL-3-(4-PYRIMIDINYL)-5-(4-PYRIDYL)-1,2,4-TRIAZOLE and 1-METHYL-3-(4-PYRIDYL)-5-(4-PYRIMIDINYL)-1,2,4-TRIAZOLE To 3-(4-pyrimidinyl)-5-(4-pyridyl)-1,2,4-triazole (2.2 g.) in dry tetrahydrofuran (125 ml.) is added 57% sodium hydride in mineral oil (0.46 g.). After refluxing 0.5 hour, methyliodide (1.4 g.) is added and the mixture is heated an additional 3 hours at reflux. The reaction mixture is cooled, filtered and concentrated to a solid. The solid is triturated with water and filtered to yield a mixture of 1-methyl-3-(4-pyrimidinyl)-5-(4-pyridyl)-1,2,4-triazole, and 1-methyl-3-(4-pyridyl)-5-(4-pyrimidinyl)-1,2,4-triazole.

EXAMPLE 32

1-BENZYL-3,5-bis(4-PYRIMIDINYL)-1,2,4-TRIAZOLE

To 3,5-bis(4-pyrimidinyl)-1,2,4-triazole (4.5 g.) in dry tetrahydrofuran (200 ml.) is added 57% sodium hydride in mineral oil (0.93 g.). The mixture is heated at reflux for 45 minutes, cooled and concentrated to a solid which is then dissolved in N,N-dimethylformamide (70 ml.). Benzylchloride (2.8 g.) is added and the solution is heated for four hours on a steam bath. The reaction mixture is concentrated to a gum, water is added and the resulting solid is removed by filtration. After recrystallization substantially pure 1-benzyl-3,5-bis(4-pyrimidinyl)-1,2,4-triazole is obtained.

EXAMPLE 33

1-METHYL-3,5-bis(4-PYRIMIDINYL)-1,2,4-TRIAZOLE

To 3,5-bis(4-pyrimidinyl)-1,2,4-triazole (2.3 g.) in dry tetrahydrofuran (125 ml.) is added 57% sodimm hydride in mineral oil (0.46 g.). After refluxing 0.5 hour, methyl iodide (1.4 g.) is added and the mixture is heated at reflux an additional 3 hours. The reaction mixture is cooled, filtered and concentrated to a solid which after recrystallization yields substantially pure 1-methyl-3,5-bis(4-pyrimidinyl)-1,2,4-triazole.

EXAMPLE 34

1-CARBAMOYL-3-(4-PYRIMIDINYL)-5-(4-PYRIDYL)-1,2,4-TRIAZOLE and 1-CARBAMOYL-3-(4-PYRIDYL)-5-(4-PYRIMIDINYL)-1,2,4-TRIAZOLE To 3-(4pyrimidinyl)-5-(4-pyridyl)-1,2,4-triazole (4.5 g.) in dry tetrahydrofuran (20 ml.) is added 57% sodium hydride in mineral oil (0.93 g.). The mixture is heated at reflux for 0.5 hour, cooled and a saturated solution of phosgene in tetrahydrofuran (50 ml.) is added dropwise with stirring at room temperature. After one hour the solution is concentrated to one-half volume and added dropwise to a saturated solution of ammonia in ethanol (100 ml.). After one hour the mixture is concentrated to a solid, aqueous sodium carbonate solution is added and the resulting solid filtered to yield a mixture of 1-carbamoyl-3-(4-pyrimidinyl)-5-(4-pyridyl)-1,2,4-triazole and 1-carbamoyl-3-(4-pyridyl)-5-(4-pyrimidinyl)-1,2,4-triazole.

Any departure from the above description which conforms to the present invention is intended to be included within the scope of the claims.

What is claimed is:
1. A compound of the formula:

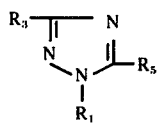 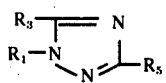

and non-toxic salts thereof, wherein

R₁ is hydrogen, $C_{1-5}$ alkyl, $C_{2-5}$ alkanoyl, phenyl -$C_{1-5}$ alkyl, carbamoyl $C_{1-5}$ alkylcarbamoyl or di -$C_{1-5}$ alkylcarbamoyl;

R₃ is pyridylmethyl, N-oxide pyridylmethyl, pyrazinyl, pyrazinyl-N-oxide, pyridazinyl or pyridazinyl-N-oxide; and R₅ is pyridyl, pyridyl-N-oxide, pyrazinyl or pyrazinyl-N-oxide such that when R₅ is a pyridyl, R₃ is other than a pyridyl.

2. A compound of the formula:

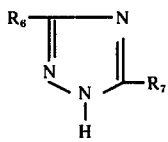

and the non-toxic pharmacologically acceptable salts thereof, wherein R₆ is pyrazinyl, or pyridazinyl and R₇ is pyridyl, or pyrazinyl.

3. A compound of the formula:

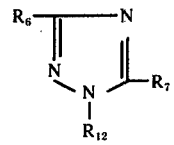

and the non-toxic pharmacologically acceptable salts thereof, wherein R₆ is pyrazinyl, or pyridazinyl and R₇ is pyridyl, or pyrazinyl and R₁₂ is $C_{1-5}$ alkyl.

4. The compound of claim 3 wherein R₁₂ is methyl.

5. A compound of the formula:

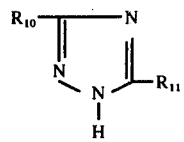

and the alkali metal and alkaline earth metal salts thereof, wherein R₁₀ is pyrazinyl or pyridazinyl and R₁₁ is pyridyl.

6. The compound of claim 5 wherein R₁₁ is 4-pyridyl.
7. The compound of claim 5 wherein R₁₀ is pyrazinyl.
8. 3-Pyrazinyl-5-(4-pyridyl)-1,2,4-triazole.
9. 5-(4-Pyridyl)-3-(4-pyridazinyl)-1,2,4-triazole.

* * * * *